United States Patent [19]

Harandi et al.

[11] Patent Number: 4,777,316
[45] Date of Patent: Oct. 11, 1988

[54] MANUFACTURE OF DISTILLATE HYDROCARBONS FROM LIGHT OLEFINS IN STAGED REACTORS

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 118,926

[22] Filed: Nov. 10, 1987

[51] Int. Cl.$^4$ .............................................. C07C 2/02
[52] U.S. Cl. .................................... 585/517; 585/533; 585/716; 585/722
[58] Field of Search ................. 585/517, 533, 716, 722

[56] References Cited

U.S. PATENT DOCUMENTS

| | | | |
|---|---|---|---|
| 3,845,150 | 10/1974 | Yan et al. | 260/673.5 |
| 3,960,978 | 6/1976 | Givens et al. | 260/683.15 |
| 4,090,949 | 5/1978 | Owen et al. | 208/78 |
| 4,417,086 | 11/1983 | Miller | 585/530 |
| 4,423,268 | 12/1983 | Miller | 585/533 |
| 4,456,779 | 6/1984 | Owen et al. | 585/415 |
| 4,542,247 | 9/1985 | Chang et al. | 585/254 |
| 4,605,807 | 8/1986 | Mazurek | 585/517 |

FOREIGN PATENT DOCUMENTS

WO85/05102  11/1985  PCT Int'l Appl.

*Primary Examiner*—Curtis R. Davis
*Attorney, Agent, or Firm*—Alexander J. McKillop; Michael G. Gilman; L. G. Wise

[57] ABSTRACT

A semi-continuous multi-stage catalytic technique for converting lower olefinic feedstock to heavier liquid hydrocarbon product. The invention provides methods and means for: (a) contacting alkene-rich feedstock at high space velocity elevated temperature in a continuous primary stage reaction zone with shape selective medium pore zeolite oligomerization catalyst particles to convert at least a portion of the lower olefinic components to intermediate olefinic hydrocarbons, said primary stage catalyst having an average acid cracking activity of about 0.1 to 20; (b) cooling primary stage oligomerization reaction effluent from the primary stage reaction zone to condense at least a portion of the intermediate hydrocarbons, separating the cooled and partially condensed primary reactor effluent stream in a primary phase separation zone into a light gas phase stream comprising light hydrocarbons and a condensed liquid intermediate hydrocarbon stream; and (c) contacting at least an intermediate effluent portion from the primary stage with shape selective medium pore zeolite oligomerization catalyst in a high pressure fixed bed secondary stage distillate mode catalytic reactor system at elevated temperature and high pressure to provide a heavier hydrocarbon effluent stream comprising distillate hydrocarbons, said secondary stage catalyst having an acid cracking activity of at least 5. A simplified second stage reactor system permits the use of one or more fixed bed reactors to be operated intermittently.

20 Claims, 3 Drawing Sheets

MANUFACTURE OF DISTILLATE HYDROCARBONS FROM LIGHT OLEFINS IN STAGED REACTORS

BACKGROUND OF THE INVENTION

This invention relates to a process and operating system for upgrading light olefins to liquid hydrocarbons. In particular, it provides a semi-continuous process for producing distillate range fuel products by oligomerizing olefinic feedstock to produce distillate product for use as diesel fuel or the like. It provides a technique for oligomerizing lower alkene-containing light gas feedstock, optionally containing ethene, propene, and/or butylenes, to produce predominantly $C_{10}+$ distillate hydrocarbons and a minor amount of olefinic gasoline and other useful products.

Developments in zeolite catalysis and hydrocarbon conversion processes have created interest in utilizing olefinic feedstocks for producing $C_5+$ gasoline, diesel fuel, distillates, lubricant stocks, etc. In addition to basic chemical reactions promoted by ZSM-5 type zeolite catalysts, a number of discoveries have contributed to the development of new industrial processes. These are safe, environmentally acceptable processes for utilizing feedstocks that contain lower olefins, especially $C_2$–$C_4$ alkenes. Conversion of $C_2$–$C_4$ alkenes and alkanes to produce aromatics-rich liquid hydrocarbon products were found by Cattanach (U.S. Pat. No. 3,760,024) and Yan et al (U.S. Pat. No. 3,845,150) to be effective processes using the ZSM-5 type zeolite catalysts. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062, 4,211,640 and 4,227,992. The above-identified disclosures are incorporated herein by reference.

Conversion of lower olefins, especially ethene, propene and butenes, over HZSM-5 is effective at moderately elevated temperatures and pressures. The conversion products are sought as liquid fuels, especially the $C_5+$ hydrocarbons. Product distribution for liquid hydrocarbons can be varied by controlling process conditions, such as temperature, pressure and space velocity. Olefinic gasoline (e.g., $C_5$–$C_9$) is readily formed at elevated temperature (e.g., up to about 350° C.) and moderate pressure from ambient to about 5500 kPa, preferably about 250 to 2900 kPa. Under appropriate conditions of catalyst activity, reaction temperature and space velocity, predominantly olefinic gasoline can be produced in good yield and may be recovered as a product or fed to a high pressure reactor system containing high acid acitivity catalyst for further conversion to heavier hydrocarbons, especially $C_{10}$–$C_{20}$ distillate-range products. Distillate mode operation can be employed to maximize production of $C_{10}+$ aliphatics by reacting the lower and intermediate olefins at high pressure and moderate temperature. Operating details for typical olefin oligomerization units are disclosed in U.S. Pat. Nos. 4,456,779; 4,497,968 (Owen et al.) and U.S. Pat. No. 4,433,185 (Tabak), incorporated herein by reference. At moderate temperature and relatively high pressure, the conversion conditions favor production of distillate-range product having a normal boiling point of at least 165° C. (330° F.). Lubricants can be manufactured by multistage reactors according to U.S. Pat. Nos. 4,520,215 and 4,568,786 (Chen and Tabak). Lower olefinic feedstocks containing $C_2$–$C_4$ alkenes may be converted selectively. While propene and butene may be converted to the extent of 50% to 99% at moderate temperature, only about 10% to 30% of ethene will be converted using only HZSM-5 or similar process conditions and acid zeolites.

It has been found that olefinic light gas rich in $C_3$–$C_4$ alkene can be upgraded to intermediate dimer and trimer liquid hydrocarbons rich in heavier $C_6$–$C_{12}$ olefinic hydrocarbons by catalytic conversion in a fixed bed or turbulent fluidized bed of solid acid zeolite catalyst at a high space velocity and under controlled reaction severity conditions to prevent substantial formation of aromatics. This technique is particularly useful in a two-stage process for upgrading olefinic components of LPG and FCC light gas. Typical feedstock may contain significant amounts of ethene, propene, butenes, $C_2$–$C_4$ paraffins and hydrogen produced in cracking heavy petroleum oils or the like. It is a primary object of the present invention to provide a novel technique for upgrading such lower olefinic feedstock to heavier lubricants, distillate and gasoline range hydrocarbons in an economic multistage reactor system.

SUMMARY OF THE INVENTION

An improved multistage catalytic process has been found for conversion of light olefinic gas feedstock, especially olefinic light gas comprising $C_3$–$C_4$ alkene, usually about 50 to 80 wt %. The main product includes distillate and/or lubricant range hydrocarbons rich in $C_{10}+$ isoolefins. The process includes the steps of: maintaining in a low severity continuous primary reaction stage a catalyst bed of zeolite particles, usually at a temperature of about 260° to 430° C. and relatively high space velocity (e.g., WHSV=0.5–80). The primary stage catalyst preferably is a fluidized bed having a particle size range of about 1 to 150 microns, an average catalyst particle size of about 20 to 100 microns, and contains about 10 to 25 weight percent of fine particles having a particle size less than 32 microns. Hot feedstock vapor can be passed upwardly through the fluidized catalyst bed in a single pass at reaction severity conditions sufficient to convert feedstock alkenes predominantly to intermediate range olefins in the $C_5$–$C_{12}$ range without substantial formation of aromatics. The primary reactor effluent contains a major amount of $C_5+$ hydrocarbons and a minor amount of $C_4-$ hydrocarbons. Light gas components can be removed from the primary effluent stream to provide an intermediate hydrocarbon stream comprising a large amount of intermediate $C_6+$ olefins along with unconverted LPG, etc. By further oligomerizing the intermediate olefins and uncoverted light olefins in the intermediate stream in a single train secondary stage high pressure reaction zone under moderate reaction temperature conditions in contact with a fixed bed of medium pore shape selective acid oligomerization catalyst having relatively high activity, the intermediate hydrocarbons are further upgraded to $C_{10}+$ hydrocarbons, including distillate product. The second stage catalytic reactor can be operated intermittently to receive intermediate olefins directly from primary stage recovery or from gasoline storage, with periodic shutdown to permit catalyst regeneration in the single train reactor.

Another major advantage of utilizing the primary stage upstream of the second stage reactor is significant reduction in the second stage regeneration frequency due to removal of the feed contaminants upstream of the second stage by the primary stage catalyst. This permits processing high contaminant concentration feed and/or eliminating the need for hydrogen circulation for maintaining the second stage catalyst activity. In addition, by using a single reactor in the second stage the secondary unit operating range of temperature may be significantly increased. Since a large part of the total process reaction coke is laid on the primary stage catalyst, second stage regeneration frequency is reduced. Based on these operation features, second stage reaction regeneration can be performed in situe or off-site regeneration may be employed.

THE DRAWINGS

DESCRIPTION OF PREFERRED EMBODIMENTS

In this description, metric units and parts by weight are employed unless otherwise stated.

The preferred feedstock contains $C_3$-$C_4$ alkenes, such as mono-olefinic propene and butenes, wherein the total $C_3$-$C_4$ alkenes are in the range of about 50 to 80 wt %. Non-deleterious components, such as methane, ethane and other paraffins and inert gases, may be present. A particularly useful feedstock is a light gas by-product of FCC gas oil cracking units containing typically 10-40 mol % $C_2$-$C_4$ olefins and 5-35 mol % $H_2$ with varying amounts of $C_1$-$C_3$ paraffins and inert gas, such as $N_2$. The process may be tolerant of a wide range of lower alkanes, from 0 to 95%. Preferred feedstocks contain more than 50 wt. % $C_1$-$C_4$ lower aliphatic hydrocarbons, and contain sufficient olefins to provide total olefinic partial pressure of at least 50 kPa. Under the reaction severity conditions employed in the present invention lower alkanes especially propane, may be partially converted to $C_4$+ products. Another useful feedstock is FCC light naphtha, which contains a relatively high concentration of pentenes, hexenes and heptenes; but, often these cannot be economically processed in a conventional fixed bed distillate mode production unit due to high concentration of catalyst poisons including basic nitrogen. Utilizing a primary stage fluid bed reactor upstream of the high pressure fixed bed reactor acts as a guard chamber which removes the contaminants from the feed on the catalyst which is continuously regenerated and catalyst activity is restored.

The primary reactor configuration may be fixed bed, fluid bed, riser type or moving bed. Although the fixed bed regeneration system can be combined with the second stage regeneration section and the second stage permanently deactivated catalyst can be used in the primary stage reactor as fresh catalyst; the fluid bed configuration for primary stage is most preferred. The main advantages of the fluid bed configurations are its flexibility for running various feedstock and temperature control.

Multistage System Operation

Figure 1:
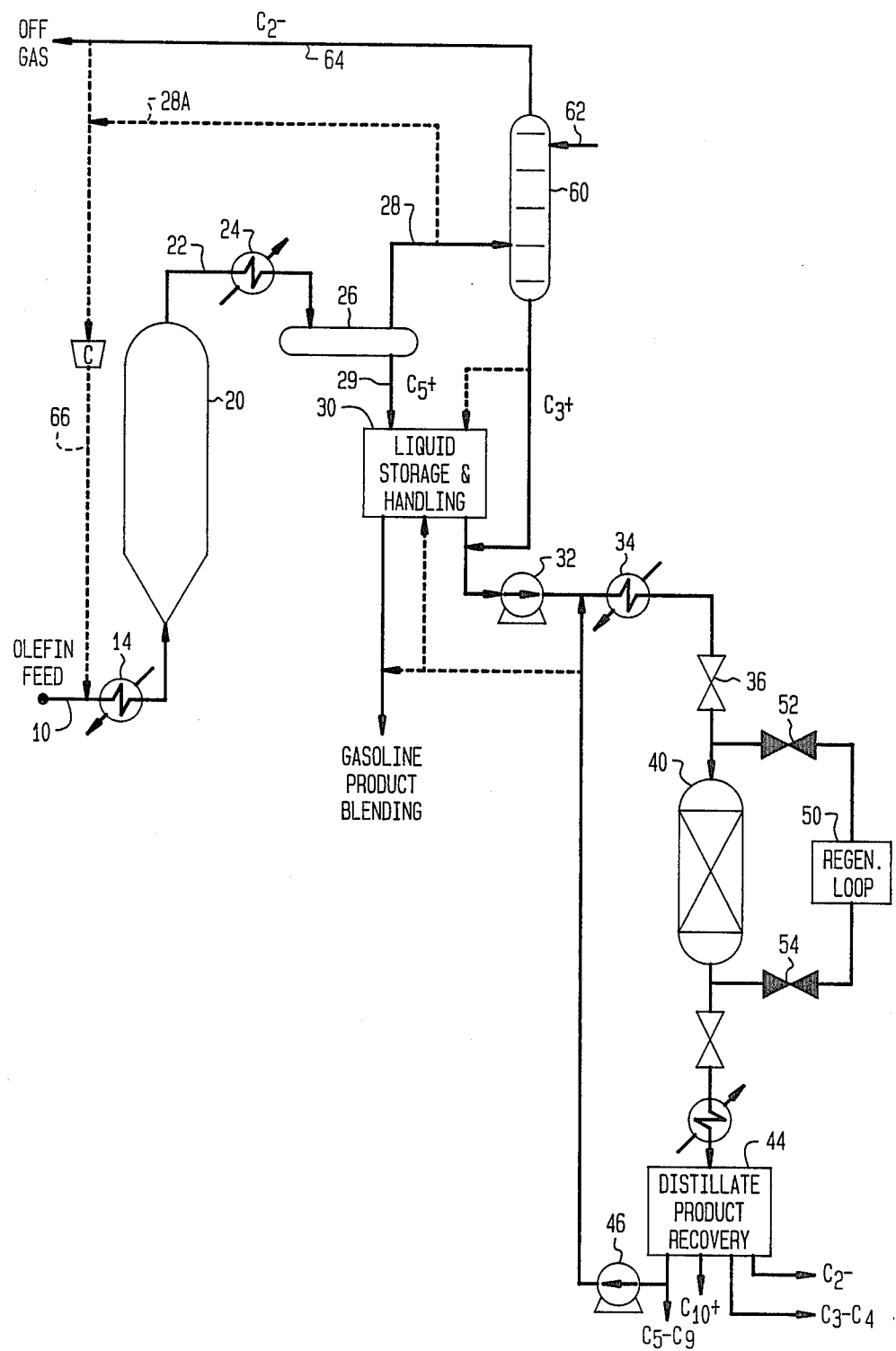
FIG. 1 is a process flow diagram depicting the overall process unit operations.

In FIG. 1 a typical multistage olefins upgrading system is depicted by a schematic process diagram. The olefin feedstock is introduced via inlet conduit 10 and heat exchanger 14 to the bottom inlet of primary stage reactor mean 20. A preferred reactor design is shown in detail in FIG. 2. Hot effluent gas passes via conduit 22 to condenser cooler means 24, wherein a major potion of the $C_5$-$C_9$ intermediate hydrocarbons are condensed and separated in phase separator unit 26 to provide a light gas stream 28, rich in unreacted $C_4-$ aliphatics, and a condensed olefinic liquid stream 29 containing a major amount of olefinic dimer and trimer components and substantially free of aromatic components, i.e.—less than 1 wt %. Liquid storage and handling means 30 is operatively connected between stages to receive, store and dispense liquid hydrocarbons within the system. During continuous production of distillate with both stages upgrading olefins, the condensed liquid hydrocarbons are withdrawn from storage and/or taken directly from upstream processing units via pump means 32 and passed through heat exchanger 34, and valve means 36 to secondary stage reactor means 40, where the hot intermediate stream is further upgraded to distillate product in contact with a fixed bed of oligomerization catalyst. The secondary stage reaction zone is maintained in distillate operating mode at moderately elevated temperature and high pressure favorable to formation of $C_{10}+$ aliphatic product. The secondary stage effluent stream is cooled in exchanger 42 and passed to product separation and recovery means 44. A liquid stream rich in $C_6$-$C_{12}$ hydrocarbons may be repressurized by pump means 46 and recycled in mixture with fresh intermediate olefins from the primary stage. Alternatively, this intermediate stream from the secondary effluent can be diverted to liquid storage means 30 or transported to gasoline product recovery or a blending unit.

Secondary reactor 40 may be single adiabatic reactor or plurality of serially connected beds with inter-bed cooling, as described in U.S. Pat. No. 4,456,779 (Owen et al), incorporated by reference. This prior patent also gives details of equipment and regeneration operation for oxidative regeneration of a typical fixed bed reactor system. This portion of the system is indicated schematically as regeneration loop 50 including valve means 52, 54 and 36 operatively connected between the primary and secondary stages and regeneration loop for periodically interrupting primary effluent flow to the secondary stage reactor 40 and connecting the secondary reactor with the regeneration loop while the fixed bed reactor is out of service. During this period the primary reactor product may be sent to the recovery section 44 to stabilize the $C_5+$ gasoline for blending. If the primary stage $C_5+$ gasoline is to be blended into the gasoline pool it is proposed to reduce the primary stage WHSV and/or increase catalyst activity to maximize the product octane. This shows another advantage of using a fluid bed as the primary stage which provides flexibility to change catalyst activity and WHSV in an economic manner. This allows efficient switching from maximum distillate to gasoline mode operation.

The present system is flexible in the regard to composition of feedstock and conversion. Advantageously, the gaseous primary effluent components are separated from the $C_5+$ rich liquid stream in phase separator unit 26 and passed via conduit 28 to absorber unit 60 where a liquid hydrocarbon sorbent stream 62 contacts the vapor to selectively sorb unreacted propene, butenes and other $C_3+$ vapor components for further reaction in the second stage. The sorbent stream 62 may be part of all of the gasoline recycle stream. The sorbate stream may be sent to storage optionally or sent directly to the secondary stage with other $C_{5+}$ liquid via pump 32. Light gas stream 64, containing $C_2$ and lighter gaseous components may be removed from the system as off gas for fuel, or part of it may be recycled via compressor line 66 to the primary stage reactor 20. Although it is often most advantageous and economic to operate the primary stage reactor as a single pass unit, recycle of unreacted $C_4-$ may be considered as an optional processing technique. Depending on the feed composition it may be advantageous to operate the primary stage at a pressure higher than the second stage reactor so that the primary stage reactor effluent is cooled in exchanger 24 and sent to the second stage reactor without separating the light components (i.e. ethane) from the second stage reactor feed. The primary stage phase diagram indicates no liquid formation in the primary stage at high operating pressures due to the relatively high temperature operation of the primary stage which is well above the critical temperature of the feed and product stream. In this alternative case separator 26 and tower 60 are eliminated. Other interstage processing equipment and operating steps are fully described in U.S. Pat. No. 4,497,968 (Wright et al).

Description of Catalysts

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalysts preferred for use herein include the medium pore (i.e., about 5-7A) shape-selective crystalline aluminosilicate zeolites having a silica-to-alumina ratio of at least 12, a constraint index of about 1 to 12 and significant Bronsted acid activity. In the primary stage reactor the coked catalyst preferably have an acid activity (alpha value) of about 0.1 to 20 under steady state process conditions to achieve the required degree of reaction severity. The second stage catalyst is generally more active (e.g.—alpha value of 10-200 or higher). Representative of the ZSM-5 type zeolites are ZSM-5, ZSM-11, ZSM-12, ZSM-22, ZSM-23, and ZSM-35. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245 and 4,046,839; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of crystalline aluminosilicate having the structure of ZSM-5 zelite with 5 to 95 wt. % silica, clay and/or alumina binder.

These siliceous zeolites may be employed in their acid form, ion exchanged or impregnated with one or more suitable metals, such as Ga, Pd, Zn, Ni, Co and/or other metals of Periodic Groups III to VIII. Ni-exchanged or impregnated catalyst is particularly useful in converting ethene under low severity conditions. The zeolite may include other components, generally one or more metals of group IB, IIB, IIIB, VA, VIA or VIIIA of the Periodic Table (IUPAC). Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligoeerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone. Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred.

Catalyst versatility permits similar zeolites to be used in both the primary stage and distillate mode secondary oligomerization stage. While it is within the inventive concept to employ substantially different catalysts in these stages, it is advantageous to employ a standard ZSM-5, suitability modified. In the description of preferred embodiments primary stage fluidized bed catalyst particles consist essentially of 25% H-ZSM-5 catalyst contained within a silica-alumina matrix and having a fresh alpha value of less than about 100, based on total catalyst weight. The secondary stage catalyst may consist of a standard 70:1 aluminosilicate H-ZSM-5 extrudate having an acid value of at least 5 preferably 150 or higher.

Stage I—Primary Stage Operation

The preferred primary stage reactor is a fluidized reactor system operating under turbulent fluidization. Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A. Accordingly, the fluidization regime is controlled to assure operation between the transition velocity and transport velocity. Fluidization conditions are substantially different from those found in non-turbulent dense beds or transport beds.

Figure 3:
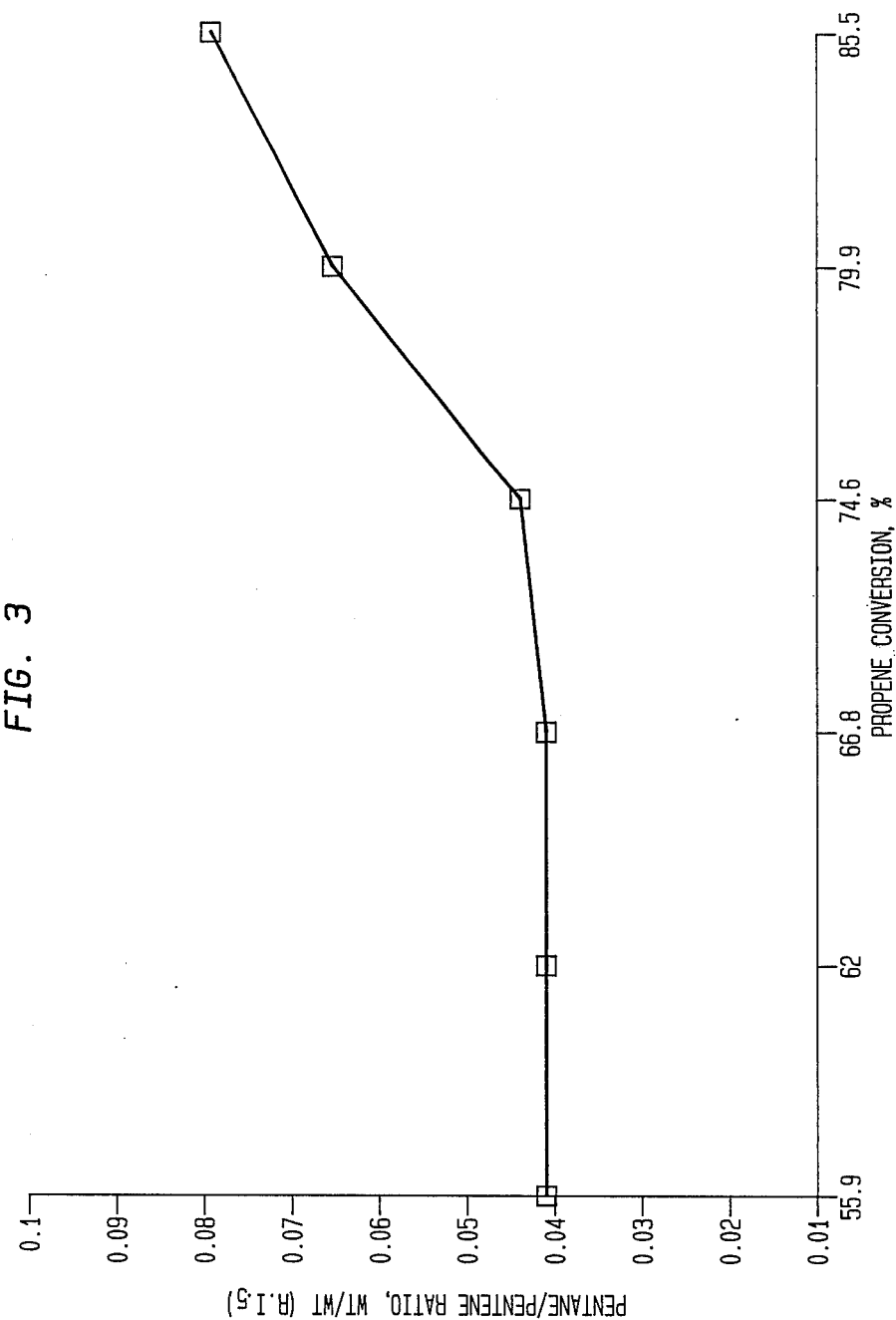
FIG. 3 is a linear plot showing olefin conversion vs. reaction severity index (R.I.).

The intermediate products are mainly $C_5$ to $C_9$ hydrocarbons, which will comprise at least 50 wt. % of the recovered product, preferably 80% or more. While olefins may be a predominant fraction of the $C_5^+$ reaction effluent, up to 99% pentenes, hexenes, heptenes, octenes, nonenes and heavier olefins; it is desired to further upgrade these intermeddates to high quality distillate containing a maximum of 1 wt % aromatics. The reaction severity index (R.I.) may be expressed in the ratio of alkane to alkene formed in the conversion. In FIG. 3 this relationship is shown for the C5 aliphatics production from conversion of propene under varying reaction severity conditions. It is noted that lower conversion rates from 50% to about 75% produce pentane and pentene in a ratio of about 0.04:1. Under these conditions very little aromatization is encountered.

The reaction severity conditions can be controlled to optimize yield of $C_5^+$ aliphatic hydrocarbons. It is understood that aromatics and light paraffin production is promoted by those zeolite catalysts having a high concentration of Bronsted acid reaction sites. Accordingly, an important criterion is selecting and maintaining catalyst inventory to provide either fresh catalyst having acid activity or by controlling primary stage catalyst deactivation and regeneration rates to provide an average alpha value of about 0.1 to 20.

Reaction temperatures and contact time are also significant factors in determining the reaction severity, and the process parameters are followed to give a substantially steady state condition wherein the reaction severity index (R.I.) is maintained within the limits which yield a desired weight ratio of alkane to alkene produced in the reaction zone, as depicted in FIG. 3. These data represent partial conversion of $C_3$ feedstock consisting essentially of propene to higher olefins over H-ZSM-5 at various levels of severity. While this index may vary from about 0.04 to 0.2, it is preferred to operate the steady state fluidized bed unit to hold the R.I. at about 0.05 to 0.1:1 corresponding to a minimum propene conversion of about 75%. While a desired conversion level of about 60 to 95% of $C_3+$ olefins can be maintained at R.I. of 0.04 or higher, corresponding ethene conversion may be only 10 to 50% over this range of operating conditions. Reaction severity is advantageously determined by the weight ratio of propane:propene in the gaseous phase, but it may also be measured by the analogous ratios of butanes:butenes, pentanes:pentenes ($CI_5$), or the average of total reactor effluent alkanes:alkenes in the $C_3$-$C_5$ range. Accordingly, the product $C_5$ ratio may be a preferred measure of reaction severity conditions, especially with $C_3$-$C_4$ mixed aliphatic feedstock containing alkanes and alkenes. In FIG. 3 these R.I. values are shown in the range of about 0.04 to about 0.08 with conversion of up to about 85% of propene feedstock in the substantial absence of added alkane in the feedstock. It is preferred to operate with $C_3$-$C_4$ conversion up to about 95% and corresponding $RI_5$ values less than 0.2. The optimum value will depend upon the exact catalyst composition, feedstock and reaction conditions; however, the typical light gas mixtures used in the examples herein and similar cracking process off-gas can be optionally upgraded to high octane aliphatic-rich gasoline by keeping R.I. above about 0.4. Operating at R.I. above 0.4 may be desirable during regeneration period of the second stage reactor in order to produce more aromatics and maximize gasoline octane if the gasoline product is used for blending.

A major advantage of the fluidized bed utilization as the primary stage reactor is adsorption of the feed contaminants on the catalyst which will be burnt in the continuous regenerator and the catalyst activity is restored. This allows conversion of high contaminant concentration feedstock such as FCC light naphtha to high quality lubes and or high quality distillate. This technique is particularly useful for operation with a fluidized catalytic cracking (FCC) unit to increase overall production of liquid product in fuel gas limited petroleum refineries. Light olefins and some of the light paraffins, such as those in FCC light gas, can be converted to valuable $C_5^+$ hydrocarbon product in a fluid-bed reactor containing a zeolite catalyst. In addition to $C_2$-$C_4$ olefin upgrading, the load to the refinery fuel gas plant is decreased considerably.

In a typical process, the olefinic feedstock is converted in a catalytic reactor under oligomerization conditions and moderate pressure (i.e.—100 to 10,000 kPa) to produce a predominantly liquid product consisting essentially of $C_5^+$ hydrocarbons rich in gasoline-range and heavier olefins and essentially free of aromatics.

Figure 2:
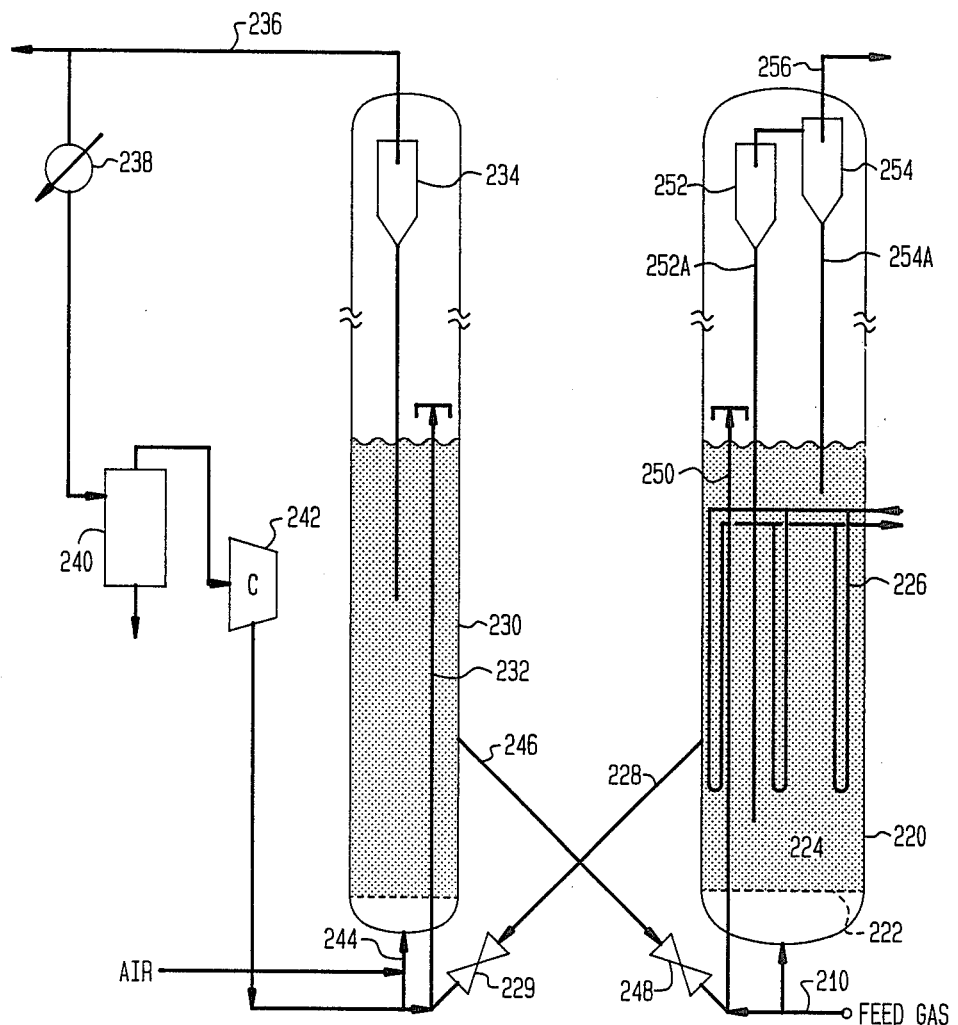
FIG. 2 is a schematic view of a fluidized bed reactor system according to the present invention.

Referring now to FIG. 2, feed gas rich in lower olefins passes under pressure through conduit 210, with the main flow being directed through the bottom inlet of reactor vessel 220 for distribution through grid plate 222 into the fluidization zone 224. Here the feed gas contacts the turbulent bed of finely divided catalyst particles. Reactor vessel 210 is shown provided with heat exchange tubes 226. The bottoms of the tubes are spaced above feed distributor grid 222 sufficiently to be free of jet action by the charged feed through the small diameter holes in the grid. Advantageously, no internal cooling coils are required whenever reaction heat can be partially or completely removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction can be controlled by adjusting feed temperature in a known manner.

Catalyst outlet means 228 is provided for withdrawing catalyst from above bed 224 and passed for catalyst regeneration in vessel 230 via control valve 229. The partially deactivated catalyst is oxidatively regenerated by controlled contact with air or other regeneration gas at elevated temperature in a fluidized regeneration zone to remove carbonaceous deposits and restore acid acitivity. The catalyst particles are entrained in a lift gas and transported via riser tube 232 to a top portion of vessel 230. Air is distributed at the bottom of the bed to effect fluidization, with oxidation byproducts being carried out of the regeneration zone through cyclone separator 234, which returns any entrained solids to the bed. Flue gas is withdrawn via top conduit 236 for disposal; however, a portion of the flue gas may be recirculated via heat exchanger 238, separator 240, and compressor 242 for return to the vessel with fresh oxidation gas via line 244 and as lift gas for the catalyst in riser 232.

Regenerated catalyst is passed to the main reactor 220 through conduit 46 provided with flow control valve 248. The regenerated catalyst may be lifted to the catalyst bed with pressurized feed gas through catalyst return riser conduit 50. Since the amount of regenerated catalyst passed to the reactor is relatively small, the temperature of the regenerated catalyst does not upset the temperature constraints of the reactor operations in significant amount. A series of sequentially connected cyclone separators 252, 254 are provided with diplegs 252A, 254A to return any entrained catalyst fines to the lower bed. These separators are positioned in an upper portion of the reactor vessel comprising dispersed catalyst phase 224. Advantageously, filters, such as sintered metal plate filters, can be used alone or conjunction with cyclones.

The product effluent separated from catalyst particles in the cyclone separating system is then withdrawn from the reactor vessel 220 through top gas outlet means 256. The recovered hydrocarbon product comprising $C_5+$ olefins and/or aromatics, paraffins and naphthenes is thereafter processed as required to provide a desired gasoline and/or higher boiling product.

Under optimized process conditions the turbulent bed may have a superficial vapor velocity of about 0.3 to 2 meters per second (m/sec). The velocity specified here is for an operation at a total reactor pressure of about 100 to 300 kPa. Those skilled in the art will appreciate that at higher pressures, a lower gas velocity may be employed to ensure operation in the turbulent fluidization regime. A convenient measure of turbulent fluidization is the bed density. A typical turbulent bed has an operating density of about 100 to 500 kg/m$^3$, preferably about 300 to 500 kg/m$^3$, measured at the bottom of the reaction zone, becoming less dense toward the top of the reaction zone, due to pressure drop and particle size differentiation. The weight hourly space velocity and uniform contact provides a close control of contact time between vapor and solid phases. The weight hourly space velocity (WHSV, based on total olefins in the fresh feedstock) is usually about 0.5 to 80 WHSV.

This process can be used with any process stream which contains sufficient light olefins and paraffins. For example, it can be used to process FCC by-product gas, which may contain about 10 to 50 wt. % total propene and butenes. The fluidized bed unit can be operated over a wide range of process variables and catalyst activity.

Fluidized Bed Reactor Operation

A typical reactor unit employs a temperature-controlled catalyst zone with indirect heat exchange and-/or adjustable gas preheat, whereby the reaction exotherm can be carefully controlled to prevent excessive temperature above the usual operating range of about 260° C. to 430° C., preferably at average reactor temperature of 300° C. to 400° C. Energy conservation in the system may utilize at least a portion of the reactor exotherm heat value by exchanging hot reactor effluent with feedstock and/or recycle streams. Advantageously, the primary reactor effluent heat may be used for the second stage reactor start up since the first reactor effluent is about 150° C. hotter than the start up second stage reactor inlet temperature. Optional heat exchangers may recover heat from the effluent stream prior to fractionation. Part of all of the reaction heat can be removed from the reactor without using the indirect heat exchange tubes by using cold feed, whereby reactor temperature can be controlled by adjusting feed temperature.

The use of a fluid-bed reactor in the primary stage offers several advantages over a fixed-bed reactor. Due to continuous catalyst regeneration, fluid-bed reactor operation will not be adversely affected by oxygenate, sulfur and/or nitrogen containing contaminants presented in the feed gas.

Stage II—Distillate Mode Oligomerization Reactor Operation

The secondary distillate production stage provides catalytic oligomerization reactor means, preferrably a fixed bed system containing medium pore shape selective acid zeolite oligomerization catalyst for converting intermediate range olefinic hydrocarbons from Stage I to liquid hydrocarbons comprising a major amount of distillate. As depicted in FIG. 1, the process intermediate feed stream from liquid storage 30, preferably comprising $C_5+$ olefinic hydrocarbons, is pressurized for a substantially different process condition by pump means 32, operatively connected as part of the fluid handling system between Stages I and II. The intermediate liquid stream is preheated by indirect heat exchange with a hot stream, such as, distillate product, in exchanger 34 and passed to the Stage II reactor 40 at a pressure of at least about 4000 kPa, preferably about 4225 to 7000 kPa (600 to 1000 psig) for light distillate production and higher pressure (e.g. 10,000 kPa) for heavy distillate or lube production.

A single train distillate mode fixed bed secondary stage reactor system is depicted. A plural reactor system may be employed with inter-reactor cooling, whereby the reaction exotherm can be carefully controlled to maximize the cycle length, based on the normal moderate temperature window of about 190° to 315° (375°–600° F.). The olefinic stream is passed through an acid medium pore zeolite bed wherein a major portion of the olefin content is converted to heavier distillate constituents. Advantageously, the space velocity (WHSV based on intermediate olefin feed) is about 0.1 to 1.5. The Stage II effluent is cooled and passed to secondary separator means 44 with appropriate distillation.

Preferably, the secondary stage reactor conditions are optimized to produce heavy liquid hydrocarbons having a normal boiling above 165° C. (330° F.). A typical secondary stage HZSM-5 fixed bed reactor system may be operated at about 0.5 to 2 liquid hourly space velocity (based on total olefins fed to reactors), temperature of 200° C. (392° F.) (SOC) to 315° C. (600° F.) (EOC) and a total pressure of 4225 kPa (600 psig), with a minimum olefin partial pressure at the inlet of about 1100 kPa (160 psig). Product fractionation is achieved by typical product fractionation systems as described in U.S. Pat. Nos. 4,456,779 and 4,504,693 (Owen et al).

It is within the inventive concept to cascade a major amount of $C_5+$ olefinic hydrocarbons directly from the primary stage into the distillate mode reactor. This will optimize the continuous process and will maximize distillate production by polymerizing olefinic gasoline boiling range components.

Table 1 shows the heat of reaction for conversion of light olefins to heavy distillate product. Conversion of hexene and heavier olefins are several times less exothermic than propene. Therefore by dimerizing and trimerizing the lower olefins in the primary stage which can operate with reaction exotherm several times higher than the second stage majority of the heat of reaction is conveniently released upstream of the second stage reactor. Since the reaction heat removal in the conventional olefins to distillate conversion is a major cost item, this significantly reduces the unit cost by reducing liquid recycle requirement and/or eliminating the need for a complicated reaction system with intercoolers, Selective dimerization and trimerization of lower olefins are possible over low activity ZSM-5 catalyst.

TABLE 1

HEAT OF REACTION FOR CONVERSION OF LIGHT OLEFINS TO HEAVY DISTILLATE

| Component | Kg Cal/Kg (BTU/LB) on Feed |
|---|---|
| Propylene | 358 (645) |
| Butylene | 233 (420) |
| Pentene | 139 (250) |
| Hexene | 94 (170) |
| Heptene | 67 (120) |

Table 2 shows that the C7+ product of the primary stage is more than 99% olefinic.

TABLE 2

Primary Stage C7+ FIMS Analysis Based on Propylene Conversion (wt %)

| CARBON NUMBER | PARAFFIN | OLEFIN | CYC-OLEFIN | DI-CYCLIC | ALKYL AROMATICS | TOTAL |
|---|---|---|---|---|---|---|
| 7 | 0.230 | 22.467 | 0.363 | 0.000 | 0.000 | 23.060 |
| 8 | 0.133 | 23.161 | 1.283 | 0.000 | 0.000 | 24.578 |
| 9 | 0.073 | 21.140 | 1.677 | 0.055 | 0.013 | 22.958 |
| 10 | 0.000 | 12.028 | 1.281 | 0.097 | 0.059 | 13.466 |
| 11 | 0.000 | 6.702 | 0.959 | 0.071 | 0.027 | 7.758 |
| 12 | 0.060 | 3.713 | 0.717 | 0.000 | 0.039 | 4.529 |
| 13 | 0.000 | 1.695 | 0.368 | 0.000 | 0.000 | 2.063 |
| 14 | 0.000 | 0.707 | 0.172 | 0.000 | 0.000 | 0.879 |
| 15 | 0.000 | 0.387 | 0.086 | 0.000 | 0.000 | 0.473 |
| 16 | 0.000 | 0.189 | 0.000 | 0.000 | 0.000 | 0.189 |
| 17 | 0.000 | 0.047 | 0.000 | 0.000 | 0.000 | 0.047 |
| 18 | 0.000 | 0.000 | 0.000 | 0.000 | 0.000 | 0.000 |
| TOTAL | 0.496 | 92.237 | 6.906 | 0.223 | 0.138 | 100 wt % |

A typical product distribution based on FCC LPG feedstock comprising predominantly $C_3$–$C_4$ olefins to the primary stage is shown in Table 3. These data are based on H-ZSM-5 catalyst having an alpha value of 3 at an average reactor temperature of 357° C. (675° F.) at WHSV=10. Partial pressure of olefin is 450 kPa (65 psia,) and olefin conversion is about 85%.

TABLE 3

| | Primary Stage Product Distribution, wt % | |
|---|---|---|
| | FCC LPG Feed | Primary Stage Product |
| $C_2=$ | — | 0.2 |
| $C_3=$ | 25.5 | 10.0 |
| $C_3$ | 7.6 | 8.2 |
| $C_4=$ | 43.7 | 9.9 |
| $C_4$ | 23.2 | 24.0 |
| $C_5$–$C_{10}$ | — | 45.2 |
| $C_{11}^+$ | — | 2.5 |

Table 4 compares the overall product yields of the inventive process versus conventional process based on FCC propene and butene conversion, the same total ZSM-5 catalyst weight used and the same liquid recycle rate of 2:1 based on fresh feed. The gasoline and distillate yield is unchanged but the distillate:gasoline selectivity ratio (D/G) is improved by about 8%.

TABLE 4

Product Distribution Comparison Based on Computer Simulation Results, wt. %

| | Conventional Process | Proposed* Process |
|---|---|---|
| $C_2=$ | 0.0 | 0.1 |
| $C_3=$ | 0.1 | 0.0 |
| $C_3$ | 8.3 | 8.6 |
| $C_4=$ | 1.2 | 0.7 |
| $C_4$ | 24.6 | 24.9 |
| $C_5$–$C_{10}$ | 35.6 | 34.3 |
| $C_{11}^+$ | 30.2 | 31.4 |

*Based on primary stage conditions of 675° F. (375° C.), 65 psia (450 Kpa) olefin partial pressure, 10 WHSV and 3 alpha ZSM-5.

While the invention has been shown by describing preferred embodiments of the process, there is no intent to limit the inventive concept, except as set forth in the following claims.

We claim:

1. A semicontinuous multistage catalytic process for conversion of light olefinic gas feedstock, comprising $C_3$–$C_4$ hydrocarbons and having an alkene content of at least about 10 wt %, to distillate range hydrocarbons rich in C10+ aliphatics, comprising the steps of maintaining a fluidized bed of medium pore acid zeolite catalyst particles in a primary reaction stage in a turbulent reactor bed maintained under reaction severity conditions effective to convert a major amount of $C_3$–$C_4$ olefins at a temperature of about 260° to 430° C., said catalyst having an average catalyst particle size of about 20 to 100 microns and average acid cracking activity of about 0.1 to 20;

passing hot feedstock vapor upwardly through the fluidized catalyst bed in a single pass at reaction severity conditions sufficient to convert at least 60% of $C_3$–$C_4$ feedstock alkene substantially to intermediate range olefins in the C5–C9 range;

maintaining fluidized bed conditions through the reactor bed at a superficial fluid velocity of about 0.3 to 2 meters per second and a weight hourly space velocity of about 0.5 to 80 parts of alkene per part by weight of fluidized catalyst;

recovering primary effluent containing a major amount of $C_5^+$ hydrocarbons, with pentane and pentene in weight ratio up to about 0.2:1, and a minor amount of $C_4-$ hydrocarbons;

recovering from the primary effluent stream an intermediate hydrocarbon stream comprising a major amount of $C_5+$ intermediate olefins;

further oligomerizing at least the $C_5+$ olefins in the intermediate stream in an intermittently operated secondary stage high pressure reaction zone under low temperature and high pressure conditions in contact with a fixed bed of medium pore shape selective acid oligomerization catalyst to further upgrade intermediate hydrocarbons to $C_{10}+$ distillate product;

periodically interrupting flow of intermediate hydrocarbons to the secondary stage reaction zone and regenerating the fixed bed catalyst while accumulating intermediate hydrocarbons from the primary zone effluent.

2. The process of claim 1 wherein the primary stage fluidized bed density is about 100 to 500 kg/m³, measured at the bottom of the bed, and wherein the primary and secondary stage catalyst comprises a siliceous metallosilicate acid zeolite having the structure of ZSM-5 zeolite.

3. The process of claim 1 wherein the primary stage feedstock consists essentially of $C_2-C_4$ light cracking gas comprising about 10 to 80 wt % total propene and butenes, and wherein the primary stage effluent is substantially free of aromatics and contains pentane and pentene in the weight ratio of about 0.04 to 0.08.

4. A multistage catalytic process for conversion of light olefinic gas feedstock consisting essentially of reactive lower alkenes to distillate range hydrocarbons rich in C10+ aliphatics, comprising the steps of maintaining a primary reaction stage containing a fluidized bed of zeolite catalyst particles in a low severity reactor bed at oligomerization temperature;

passing hot olefinic feedstock vapor upwardly through the fluidized catalyst bed in a single pass at reaction severity conditions sufficient to upgrade the lower alkenes to intermediate range olefins mainly in the $C_5-C_{12}$ range;

recovering primary effluent containing a major amount of $C_5+$ *hydrocarbons, less than* 1 wt % aromatics and a minor amount of $C_4-$ hydrocarbons;

removing substantially light gas components from the primary effluent stream to provide an intermediate hydrocarboon stream comprising a major amount of intermediate olefins; and further oligomerizing the $C_5+$ olefins in the intermediate stream in a single reactor train secondary stage high pressure reaction zone in contact with at least one fixed bed of medium pore shape selective acid oligomerization catalyst to further upgrade intermediate hydrocarbons to C10+ distillate product.

5. The process of claim 4 wherein primary stage fluidized catalyst has a size range of about 1 to 150 microns, average catalyst particle size of about 20 to 100 microns, and containing about 10 to 25 weight percent of fine particles having a particle size less than 32 microns.

6. The process of claim 4 wherein the primary stage catalyst has an acid cracking value of about 0.1 to 20 and the space velocity is about 0.5-80 WHSV, based on primary reactor fluidized catalyst weight.

7. The process of claim 4 comprising the further step of withdrawing a portion of coked catalyst from the primary stage fluidized bed reactor, oxidatively regenerating the withdrawn catalyst and returning regenerated catalyst to the primary stage reactor at a rate to control catalyst activity whereby $C_3-C_5$ alkane:alkene weight ratio in the hydrocarbon product is maintained at about 0.04:1 to 0.2:1 under conditions of reaction severity to effect feedstock conversion.

8. The process of claim 4 wherein the primary stage catalyst consists essentially of a medium pore pentasil zeolite having an acid cracking value of about 0.1 to 20 and average particle size of about 20 to 100 microns; fluidized bed reactor catalyst inventory includes at least 10 weight percent fine particles having a particle size less than 32 microns; and wherein the catalyst particles comprise about 5 to 95 weight percent ZSM-5 metallosilicate zeolite having a crystal size of about 0.02–2 microns.

9. The process of claim 4 wherein secondary stage single reactor train oligomerization zone operation is periodically interrupted to permit regeneration of secondary stage catalyst.

10. The process of claim 9 wherein the secondary stage reactor train is operatively connected to a regeneration loop during periodic interruption thereby providing a catalyst regenerating stream to the secondary stage reactor train.

11. The process of claim 4 wherein the feedstock includes up to 80 wt. % of propene.

12. A multi-stage catalytic process for converting lower olefinic feedstock to heavier liquid hydrocarbon product, comprising the steps of contacting propene-rich feedstock at elevated temperature in a continuous primary stage reaction zone with shape selective medium pore zeolite oligomerization catalyst to convert at least 75% of propene to $C_5+$ intermediate olefinic hydrocarbons under reaction severity conditions sufficient to produce pentane and pentene in a weight ratio of about 0.05 to 2:1, said primary stage catalyst having an average acid cracking activity of about 0.1 to 20;

cooling primary stage oligomerization reaction effluent from the primary stage reaction zone to condense at least a portion of the intermediate hydrocarbons, separating the cooled and partially condensed primary reactor effluent stream in a primary phase separation zone into a light gas phase stream comprising light hydrocarbons and a condensed liquid intermediate hydrocarbon stream; and contacting at least an intermediate effluent portion from the primary stage with shape selective medium pore zeolite oligomerization catalyst in a high pressure secondary stage low severity catalytic reaction zone at moderate temperature and high pressure to provide a heavier hydrocarbon effluent stream comprising distillate hydrocarbons, said secondary stage catalyst having an acid cracking activity of at least 5.

13. The process of claim 12 wherein the liquid intermediate stream comprises at least 75 mole % $C_5$ to $C_{12}$ aliphatic hydrocarbons.

14. The process of claim 12 wherein the feedstock comprises at least 10 mole % propene.

15. The process of claim 12 wherein the feedstock consists essentially of $C_3-C_4$ olefins and wherein the catalyst in both stages comprises at least one zeolite having the structure of ZSM-5.

16. The process of claim 12 wherein said primary and secondary stages include fixed bed reactors, including at least one standby reactor to permit continuous operation during regeneration of at least one stage reactor.

17. A semicontinuous multistage catalytic process for conversion of light olefinic gas feedstock, comprisng $C_3$–$C_4$ hydrocarbons and having an alkene content of at least about 10 wt %, to distillate range hydrocarbons rich in C10+ aliphatics, comprising the steps of maintaining a fluidized bed of medium pore acid zeolite catalyst particles in a primary reaction stage in a turbulent reactor bed maintained under reaction severity conditions effective to convert at least 60% of $C_3$–$C_4$ olefins at a temperature of about 260° to 430° C. and weight hourly space velocity of about 0.5 to 80, based on total reactor catalyst, said catalyst having an average acid cracking activity of about 0.1 to 20;

passing hot feedstock vapor upwardly through the fluidized catalyst bed to convert $C_3$–$C_4$ feedstock olefins substantially to intermediate range olefins rich in dimers and trimers of propene and butene, with not more than 1 wt % aromatics;

recovering primary effluent containing a major amount of $C_5+$ hydrocarbons, with pentane and pentene in weight ratio of about 0.04 to 0.2:1;1 recovering from the primary effluent stream an intermediate hydrocarbon stream comprising a major amount of $C_5+$ intermediate olefins;

further oligomerizing at least the $C_5+$ olefins in the intermediate stream in an intermittently operated secondary stage high pressure fixed catalyst bed reaction zone under low temperature and high pressure conditions in contact with medium pore shape selective acid oligomerization catalyst to further upgrade intermediate hydrocarbons to predominantly $C_{10}+$ distillate product;

periodically interrupting flow of intermediate hydrocarbons to the secondary stage reaction zone and regenerating the fixed bed catalyst while accumulating intermediate hydrocarbons from the primary zone effluent.

18. The process of claim 17 wherein primary stage conversion of $C_3$–$C_4$ olefin is maintained at about 75 to 95%.

19. The process of claim 17 wherein the feedstock contains ethene and the primary stage catalyst comprises Ni-containing acid ZSM-5.

20. The process of claim 17 wherein the second stage comprises serial fixed bed adiabatic reactors with inter-reactor cooling to maintain process temperature.

* * * * *